United States Patent [19]

Holman et al.

[11] 4,239,492

[45] Dec. 16, 1980

[54] METHOD OF PREPARING VASCULAR GRAFTS OF HUMAN AND OTHER UMBILICAL CORD ORIGINS FOR TISSUE INGROWTH

[76] Inventors: Daniel G. Holman, 12743 Radisson Rd. NE., Blaine, Minn. 55434; Robert A. Ersek, 5416 Diamondhead Dr. East, Bay St. Louis, Miss. 39520; Arthur A. Beisang, 2263 Dellwood, Roseville, Minn. 55113

[21] Appl. No.: 48,381

[22] Filed: Jun. 14, 1979

Related U.S. Application Data

[63] Continuation of Ser. No. 872,606, Jan. 26, 1978, abandoned.

[51] Int. Cl.³ .................................................. C14C 1/00
[52] U.S. Cl. ................................... 8/94.11; 8/94.18; 8/94.19 C; 8/94.33
[58] Field of Search .............. 8/94.11, 94.18, 94.19 C, 8/94.33

[56] References Cited

U.S. PATENT DOCUMENTS

| | | | |
|---|---|---|---|
| 55,740 | 6/1866 | Taylor | 8/94.11 |
| 3,093,439 | 6/1963 | Bothwell | 8/94.11 |
| 3,523,027 | 8/1970 | Hall | 8/94.11 |
| 4,050,893 | 9/1977 | Hancock et al. | 8/94.11 |

OTHER PUBLICATIONS

B. P. Mindlich et al., Trans. Amer. Soc. Artif. Int. Organs, 1975, 21, pp. 273–278.

B. P. Mindlich et al., Dialysis and Transplant, Aug.-/Sep. 1976, pp. 19–20.

B. Mindlich, et al., Surgery, 1977, 81, (No. 2), pp. 152–160.

Dardick et al., J. American Medical Association, 1976, 236 (No. 25), pp. 2859–2862.

*Primary Examiner*—A. Lionel Clingman
*Attorney, Agent, or Firm*—Orrin M. Haugen; Thomas J. Nikolai

[57] ABSTRACT

A method for preparing human and other animal umbilical cords for use as a vascular replacement and/or arterial venous fistula which permits the umbilical cord which is to be grafted to be preformed into a desired predetermined configuration. The method includes roughening the surface of the umbilical cord at the point of juncture with the host tissue, external to the umbilical cord, thereby improving the sealing arrangement at said juncture to allow for puncturing of the graft as well as mechanical retention. Additionally, the method may include the steps of flushing the cord in an aqueous solution either before or after roughening, and then the flushed cord is mounted upon a mandrel having the desired configuration. The roughened and mounted cord may then be immersed in ethyl alcohol until substantially dehydrated, and thereafter fixed in an aldehyde selected from the class consisting of dialdehyde starch and gluteraldehyde, with the aldehyde fixing the roughened tissue into a shape conforming to the mandrel upon which it is mounted.

3 Claims, No Drawings

METHOD OF PREPARING VASCULAR GRAFTS OF HUMAN AND OTHER UMBILICAL CORD ORIGINS FOR TISSUE INGROWTH

This is a continuation of application Ser. No. 872,606, filed Jan. 26, 1978, now abandoned.

BACKGROUND OF THE INVENTION

The present invention relates generally to an improved method for preparing vascular replacements and/or arterial venous fistula, and particularly wherein a preformed umbilical cord is being utilized. More specifically, the method of the present invention relates to a technique for treating the umbilical cord tissue to render it more readily and securely received within the body of the host. Specifically, the surface of the umbilical cord is roughened at the point or along the surface where it is received within the host so as to be more readily and securely received, and to allow for the sealing of numerous access punctures such as are necessary when the graft is utilized for hemodialysis access.

Implantable prosthetic devices for either permanent or semi-permanent implantation into the body for the controlled passage of fluids are in relatively wide usage throughout the world. Normally, such implantable devices are utilized for treating renal failure through dialysis, or for other disorders which may be treated by frequent access to the arterial-venous system.

In order to achieve a proper implant, the material utilized must provide for a relatively sound surface seal which resists infection. It has been found that umbilical cords are well suited for this purpose, since processed umbilical cords are normally not rejected by the host, and furthermore, are reasonably accepted by the subcutaneous tissues of the patient.

Normally, the exterior surface of the umbilical cord is relatively smooth, and hence does not provide a surface to which the live tissues of the patient may readily bond. Thus a puncture site may allow bleeding into and propagation along the host/prosthesis interface producing a perigraft aneurysm. In accordance with the present invention, the exterior surface is roughened sufficiently so as to enhance the bonding capability (tissue ingrowth), with the combination of the umbilical cord and the roughness providing a desired medium for incorporation. This roughening provides a mechanical bond at the host/prosthesis interface that prevents perigraft aneurysms. The umbilical cord is normally a relatively straight tubular member, but is, of course, highly flexible. As in any flexible tubular structure of this type, bending or forming about a relatively small radius of curvature will cause kinking or buckling of the walls, with the kink resisting flow through the cord. Umbilical cords or segments thereof may be made to conform to a predetermined configuration including relatively sharp bends through a system of dehydration followed by fixing of the structure into the desired form. The details of one such fixing procedure are disclosed in our copending application executed on even date herewith entitled "METHOD OF PREFORMING VASCULAR GRAFTS OF HUMAN AND OTHER ANIMAL ORIGIN".

Artificial dialysis has been widely used since its development by Kolff. Since the development and demonstration of this procedure, efforts have been undertaken to improve the techniques of gaining access to the blood stream of the patient, with access being required on an intermittent and sometimes frequent basis. In the past, bovine carotid artery has been reasonably widely used for the cannulation of blood vessels in the arterial-venous systems for hemodialysis. While bovine carotid artery is usable for such application, it has been determined recently that human umbilical cords are preferable for certain such applications.

In an article entitled "Possible Improvements in the Technique of Long Term Cannulation of Blood Vessels", by Quinton, Dillard, Cole and Scribner, *Trans. Am. Soc. for Artif. Int. Organs*, 7:60, 1960, an ideal cannula for blood vessels was described having the following features:

(1) The inner surface exposed to the body fluids should minimize clotting thereof;
(2) The exterior surface should provide minimal tissue reaction so as to avoid rejection;
(3) The exterior surface should permit bonding or attachment to the skin or subcutaneous tissue;
(4) The skin should properly surround the cannula member for sealing;
(5) The cannula material should be reasonably flexible in the tissue contacting area;
(6) The cannula should be sufficiently flexible so as not to occlude adjacent vessels;
(7) The cannula should be sufficiently durable so as to withstand trauma without permanent deformation;
(8) The cannula should have a means to facilitate contact with various vessel sizes;
(9) Means should be provided to permit attachment by clamping or the like to the external circuit means when required; and
(10) The cannula should be arranged relatively close to the skin surface and not extend far into the subcutaneous tissue.

It has been found that processed human umbilical cords achieve most of these criteria, and are particularly well adapted to satisfy these requirements when treated in accordance with the technique of the present invention. Generally speaking, human umbilical cords, particularly when treated in accordance with the present invention, achieve a performance significantly superior to that of synthetic resinous materials such as, for example, polyethylene terephthalate (Dacron) or the like.

SUMMARY OF THE INVENTION

Generally, and in accordance with the present invention, a human umbilical cord is roughened on the outer surface by use of a wire brush, electric brush, rotary abrasive wheel, or the like. The exterior surface is perforated, with the individual separations extending through the outer membrane of the graft. The extent of roughening is preferably as complete as possible with individual perforations being spaced apart no more than one-quarter inch. The perforations and surface irregularities accommodate tissue ingrowth from the subcutaneous host tissue, thus providing a mechanical bond. Additionally, the umbilical cord is arranged or conformed to a predetermined configuration following flushing of the cord for removal of any substances from the inner and outer surfaces thereof, and thereafter mounting the cord upon a suitable mandrel having the desired configuration. While on the mandrel, the cord is then immersed in ethyl alcohol, particularly a solution having more than about 70% ethyl alcohol, and permitted to remain immersed until substantially dehydrated, the dehydration operation normally taking at least about 18 hours. Thereafter, the dehydrated cord, while remaining on the mandrel, is fixed by immersion in an aqueous solution of aldehyde selected from the group consisting of dialdehyde starch and/or gluteraldehyde, with the solution containing more than about 1% of the aldehyde. The fixing operation normally requires immersion for a period of about 18 hours or more.

Therefore, it is a primary object of the present invention to provide an improved implantable prosthetic device for transmission of body fluids, wherein the implantable material is a treated umbilical cord.

It is a further object of the present invention to provide an improved technique for preparing an umbilical cord for implantation into a patient's body, the cord being roughened for enhancing the implantation purpose.

Other and further objects of the present invention will become apparent to those skilled in the art upon a study of the following specification and appended claims.

DESCRIPTION OF THE PREFERRED EMBODIMENT

In accordance with the preferred embodiment of the present invention, the umbilical cord is provided for use as a vascular replacement or arterial venous fistula, which allows for host tissue ingrowth into the preserved cord. The host tissue ingrowth is accommodated through abrasion and roughening of the external surface of the processed umbilical cord. The abrasion of the external surface is preferably accomplished by mechanical means through the use of a wire brush, which causes disruption of the external surface of the umbilical cord, thus allowing for the host tissue ingrowth. Preferably, the abrasion is accomplished by causing the bristles of the wire brush to penetrate the outer membrane only of the cord, with the individual perforations or abrasions being spaced apart a distance of approximately one-thirty-second of an inch, and for best results, not more than one-fourth inch on center. As an alternative, a router, scraper, or sander may be utilized to achieve similar results.

Either prior to or subsequent to the abrasion operation, the human umbilical cord may be treated to achieve a desired configuration in a fixed disposition, with this desired configuration being, for example, a configuration utilizing a straight section of approximately 10 centimeters in length, at which point a 180° bend is formed having a radius of approximately 5 centimeters. A second segment extends from the bend having a length of approximately 20 centimeters forming a "J"-shaped graft. Alternatively, a segment or component is formed having a straight segment of approximately 20 centimeters followed by a 180° bend with a radius of 5 centimeters, with a leg extending from the bend of approximately 20 centimeters in length forming a "U"-shaped graft. Such a configuration is adapted for use as an implant for achieving artificial dialysis on the patient when required.

As an additional alternate, a straight graft may have the internal diameter gradually tapered from 8 mm. in diameter at the proximal opening to 3 mm. in diameter at the distal opening, thus allowing for more proper anastomosis with varying sized patient vessels. Generally speaking, it has been found more desirable to perform the roughening operation after the dehydration and fixing operations.

The grafts are flushed with deionized water by any suitable technique, such as utilization of a flexible squeeze bottle or the like. Following flushing, the cord element is slipped upon or otherwise mounted on an appropriate mandrel having a surface with good release properties. Polished polytetrafluoroethylene has been found to provide good release qualities. The mandrel has the configuration desired, such as the "J" shape described above, or a single "U" configuration. Additionally, and if desired, the mandrel may be tapered to accommodate attachment to preselected members of the arterial venous system of the patient.

While mounted on the mandrel, the cord is immersed in ethyl alcohol, with the solution containing not less than 70% by volume of ethyl alcohol, with the immersion continuing for at least 18 hours. Immersion is maintained until the cord is substantially dehydrated, with a period of 18 hours normally being required to achieve dehydration. Thereafter, the dehydrated cord, while mounted on the mandrel is immersed in an aqueous solution of dialdehyde starch, with the solution containing not less than 1% of dialdehyde starch by volume. Fixing is achieved after immersion in the dialdehyde starch solution for 18 hours.

All of the procedures involved may be accomplished at room temperature under normal conditions.

Thereafter, the preformed cord is placed in a solution containing not less than 40% ethyl alcohol and 1% propylene oxide and stored until implanting is accomplished.

As an alternative to the above example, gluteraldehyde is substituted for the dialdehyde starch with similar results being achieved. As has been indicated, immersion in ethyl alcohol for dehydration should be in alcohol solution containing more than 70% ethyl alcohol by volume. Also, the aldehyde solutions should contain at least about 1% of either dialdehyde starch or gluteraldehyde. Normally, solutions of 95% alcohol and 1.3% of dialdehyde starch or gluteraldehyde are preferred.

We claim:

1. The method of preparing an umbilical cord for implantation in a human body which method comprises the steps of:
    (a) roughening the outer surface of the cord prior to implantation, with the individual abrasions of the cord extending through the outer membrane of said cord, thus having a rough and textured surface area containing small hair-like projections;
    (b) flushing the cord and thereafter mounting the cord upon a mandrel of the desired configuration;
    (c) immersing the mounted cord and mandrel into an aqueous solution of ethyl alcohol containing more than about 70% of ethyl alcohol; and
    (d) thereafter immersing the mounted cord in an aqueous solution of aldehyde selected from the group consisting of dialdehyde starch and/or gluteraldehyde containing more than about 1% of said aldehyde in water for a period sufficiently long to permit the configuration to become fixed.

2. The method as defined in claim 1 being particularly characterized in that said cord is provided with perforations about the exterior thereof, and wherein the perforations are spaced apart by a distance less than approximately one-quarter inch.

3. The method as defined in claim 2 being particularly characterized in that said spacing is less than approximately one-thirty-second inch.

* * * * *